(12) United States Patent
Li et al.

(10) Patent No.: US 6,673,923 B2
(45) Date of Patent: Jan. 6, 2004

(54) PYRAZOLE ANTIMICROBIAL AGENTS

(75) Inventors: Leping Li, Burlingame, CA (US); Xiaoqi Chen, San Mateo, CA (US); Serena T. Cutler, Palo Alto, CA (US)

(73) Assignee: Tularik Inc., South San Francisco, CA (US)

( * ) Notice: Subject to any disclaimer, the term of this patent is extended or adjusted under 35 U.S.C. 154(b) by 33 days.

(21) Appl. No.: 09/847,962

(22) Filed: May 2, 2001

(65) Prior Publication Data

US 2002/0049205 A1 Apr. 25, 2002

Related U.S. Application Data

(60) Provisional application No. 60/201,988, filed on May 3, 2000.

(51) Int. Cl.$^7$ .............................................. C07D 231/12
(52) U.S. Cl. ..................... 544/140; 544/140; 544/371; 546/211; 548/377.1; 514/236.5
(58) Field of Search ......................... 544/140; 546/211; 514/236.5; 548/377.1

(56) References Cited

U.S. PATENT DOCUMENTS 3,200,128 A    8/1965   Wagner

*Primary Examiner*—Robert W. Ramsuer
(74) *Attorney, Agent, or Firm*—Townsend and Townsend and Crew LLP

(57) ABSTRACT

The present invention provides pyrazole and pyrazolone derivatives. Preferred compounds of the invention are useful as RNA polymerase inhibitors. Further preferred compounds of the invention are useful as antimicrobial agents.

3 Claims, No Drawings

PYRAZOLE ANTIMICROBIAL AGENTS

CROSS-REFERENCES TO RELATED APPLICATIONS

This application claims priority to U.S. patent application Ser. No. 60/201,988, filed May 3, 2000, the disclosure of which is incorporated by reference herein.

BACKGROUND OF THE INVENTION

Resistance to currently available antibiotics has created a need for new antibiotic agents. Infections, caused by organisms such as *Staphylococcus aureus, Pseudomonas aeruginosa, Enterococcus faecium* and *Enterococcus faecalis,* have become increasingly resistant to currently approved antibiotics. For example, significant clinical problems include methicillin-resistant strains of *S. aureus,* which are resistant to all current antibiotics except vancomycin (a drug of last resort because of severe side effects), and a vancomycin-resistant strain of *E. faecium enterococci,* which is now found world-wide. Even community-acquired organisms such as *Streptococcus pneumoniae* are increasingly resistant to antimicrobial agents, with a significant number of isolates being resistant to penicillin and extended-spectrum cephalosporins.

The emergence and spread of resistant bacterial organisms are primarily caused by acquisition of drug resistance genes, resulting in a broad spectrum of antibiotic resistance (e.g., extended-spectrum cephalosporin-resistant mutant β-lactamases found in several bacterial organisms). Genetic exchange of multiple-resistance genes, by transformation, transduction and conjugation, combined with selective pressures in settings such as hospitals where there is heavy use of antibiotic therapies, enhance the survival and proliferation of antimicrobial agent-resistant bacterial strains occurring by, e.g., spontaneous mutation. Although the extent to which bacteria develop resistance to antimicrobial drugs and the speed with which they do so vary with different types of drugs, resistance has inevitably developed to all antimicrobial agents (see, Gold and Moellering, Jr., 1996, *New Eng. J Med.,* 335(19):1445–1453).

To prevent or delay the buildup of a resistant pathogen population, different chemicals that are effective against a particular disease-causing bacterium must be available. Thus, there is a need to identify compounds which can penetrate and specifically kill the pathogenic bacterial cell, or arrest its growth without also adversely affecting its human, animal, or plant host.

One avenue for accomplishing this task involves the use of compounds targeting bacterial RNA polymerase. Accordingly, what is needed in the art are new compounds which are effective inhibitors of bacterial RNA polymerase and useful as antimicrobial agents. The present invention provides such compounds along with methods for their use.

SUMMARY OF THE INVENTION

In a first aspect, the present invention provides compounds having the formula:

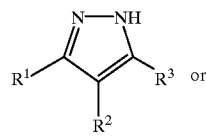 I

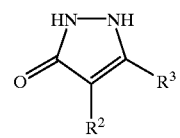 II wherein $R^1$ is selected from H, OR' and NR'R", wherein R' and R" are independently selected from H and substituted or unsubstituted lower alkyl. $R^2$ and $R^3$ are independently selected from substituted or unsubstituted aryl, substituted or unsubstitued heteroaryl, substituted or unsubstituted alkyl, substituted or unsubstituted heteroalkyl, substituted or unsubstituted heteroarylalkyl, substituted or unsubstituted heteroaryl-heteroalkyl, and substituted or unsubstituted aryl-heteroalkyl.

Unless otherwise indicated, the compounds provided in the above formulas are meant to include pharmaceutically acceptable salts and prodrugs thereof.

In another aspect, the present invention provides pharmaceutical compositions comprising a compound of formula I or II in admixture with a pharmaceutically acceptable carrier or excipient.

In still another aspect, the present invention provides methods for treating or preventing bacterial growth in a subject by administering to the subject a therapeutically effective amount of a compound of formula I or II.

In yet another aspect, the present invention provides methods for modulating bacterial growth on a surface comprising contacting the surface with a compound of formula I or II.

Other objects and advantages of the present invention will be apparent from the detailed description that follows.

DETAILED DESCRIPTION OF THE INVENTION

Abbreviations and Definitions

The abbreviations used herein are conventional, unless otherwise defined.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multi-valent radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl," "cycloalkyl" and "alkylene." The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" refer to those groups having an alkyl group attached to the remainder of the molecule through an oxygen, nitrogen or sulfur atom, respectively. Similarly, the term "dialkylamino" is used in a conventional sense to refer to —NR'R" wherein the R groups can be the same or different alkyl groups.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical.

The term "alkoxycarbonyl" denotes —C(O)OR wherein R is alkyl as defined herein.

The term "alkylcarbamoyl" denotes —C(O)NR'R" wherein R' and R" are independently selected alkyl groups as defined herein.

The term "sulfonyl" denotes —$SO_2$—.

The term "sulfamoyl" denotes —$SO_2NH_2$.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—$H_2$—$CH_2$—NH—$CH_2$—. For heteroalkylene groups, heteroatoms can also occupy either or both of the chain termini. Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2, 5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings), which are fused together or linked covalently. "Heteroaryl" are those aryl groups having at least one heteroatom ring member. Typically, the rings each contain from zero to four heteroatoms selected from N, O and S, wherein the nitrogen and sulfur atoms are optionally oxidized, and the nitrogen atom(s) are optionally quaternized. The "heteroaryl" groups can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below. The term "arylalkyl" is meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from, for example: —OR', =O, =NR', =N—OR', —NR'R", —SR', -halogen, —SiR'R"R"', —OC(O)R', —C(O)R', —$CO_2$R', CONR'R", —OC(O)NR'R", —NR"C(O)R', —NR'—C(O)NR"R"', —NR"C(O)$_2$R', —NH—C(NH$_2$)=NH, —NR'C(NH$_2$)=NH, —NH—C(NH$_2$)=NR', —S(O)R', S(O)$_2$R', —S(O)$_2$NR'R", —CN and —$NO_2$ in a number ranging from zero to (2N+1), where N is the total number of carbon atoms in such radical. R', R" and R"' each independently refer to hydrogen, unsubstituted ($C_1$–$C_8$)alkyl and heteroalkyl, unsubstituted aryl, aryl substituted with 1–3 halogens, unsubstituted alkyl, alkoxy or thioalkoxy groups, or aryl-($C_1$–$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similarly, substituents for the aryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C $(NH_2)=NH$, $-NH-C(NH_2)=NR'$, $-S(O)R'$, $-S(O)_2R'$, $-S(O)_2NR'R''$, $-N_3$, $-CH(Ph)_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl, (unsubstituted aryl)-($C_1$-$C_4$)alkyl, (unsubstituted aryl)oxy-($C_1$-$C_4$)alkyl and perfluoro($C_1$-$C_4$)alkyl.

Two of the substituents on adjacent atoms of the aryl ring may optionally be replaced with a substituent of the formula $-T-C(O)-(CH_2)_q-U-$, wherein T and U are independently $-NH-$, $-O-$, $-CH_2-$ or a single bond, and the subscript q is an integer of from 0 to 2. Alternatively, two of the substituents on adjacent atoms of the aryl ring may optionally be replaced with a substituent of the formula $-A-(CH_2)_r-B-$, wherein A and B are independently $-CH_2-$, $-O-$, $-NH-$, $-S-$, $-S(O)-$, $-S(O)_2-$, $-S(O)_2NR'-$ or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula $-(CH_2)_s-X-(CH_2)_t-$, where s and t are independently integers of from 0 to 3, and X is $-O-$, $-NR'-$, $-S-$, $-S(O)-$, $-S(O)_2-$, or $-S(O)_2NR'-$. The substituent R' in $-NR'-$ and $-S(O)_2NR'-$ is selected from hydrogen or unsubstituted ($C_1$-$C_6$)alkyl.

As used herein, the term "heteroatom" is meant to include, for example, oxygen (O), nitrogen (N), sulfur (S) and silicon (Si).

As used herein, the term "modulate" means to reduce, prevent or otherwise, control, microbial growth. The microbes whose growth is modulated include bacteria, viruses, mycobacterium, yeasts and parasites. In preferred embodiments, the microbes are bacteria. The term modulate is meant to include effects that are both cidal and static.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", *Journal of Pharmaceutical Science,* 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are substantially equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

Certain compounds of the invention may exist in one or more tautomeric forms. The present invention encompasses the various tautomeric forms of the compounds of the invention, including both single tautomers and mixtures of tautomers.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Compounds

In one aspect, the present invention provides compounds of the formula

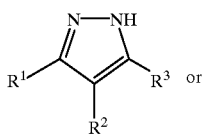
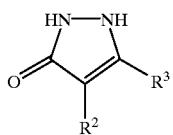

wherein R¹ is selected from H, OR' and NR'R", wherein R' and R" are independently selected from H and substituted or unsubstituted lower alkyl. $R^2$ and $R^3$ are selected from substituted or unsubstituted aryl, substituted or unsubstitued heteroaryl, substituted or unsubstituted alkyl, substituted or unsubstituted heteroalkyl, heteroarylalkyl, substituted or unsubstituted heteroaryl-heteroalkyl, and substituted or unsubstituted aryl-heteroalkyl. Preferably, when $R^2$ is a halo-susbstituted phenyl group, $R^3$ is other than a phenyl group substituted with a moiety bound to said phenyl group via a sulfur atom.

In a preferred embodiment, $R^2$ and $R^3$ are independently selected from substituted or unsubstituted aryl and substituted or unsubstitued heteroaryl groups. In this embodiment, the substituted aryl and substituted heteroaryl groups are preferably substituted with a member selected from, hydroxyl, halogen, nitro, cyano, substituted or unsubstituted $(C_1-C_6)$alkyl, $(C_1-C_6)$heteroalkyl, $(C_1-C_6)$alkoxy, $(C_1-C_6)$alkylthio, substituted or unsubstituted aryl, substituted or unsubstituted heteroaryl, —C(O)$_m$R⁴, —C(O)NR⁴R⁵, —S(O)$_n$R⁴, —SO₂NR⁴R⁵, —NR⁴R⁵, —NR⁶C(O)$_m$—R⁴, —NR⁶C(O)NR⁴R⁵, —NR⁶S(O)$_n$R⁴, —OC(O)$_m$R⁴ and —OC(O)NR⁴R⁵, wherein m is an integer independently selected from 1 and 2 and n is independently selected from the numbers from 0 to 2. $R^4$, $R^5$ and $R^6$ are independently selected from hydrogen, substituted or unsubstituted $(C_1-C_8)$alkyl, substituted or unsubstituted $(C_1-C_8)$heteroalkyl or one or more of $R^4$, $R^5$, and $R^6$ is substituted or unsubstituted $(C_3-C_6)$alkyl or substituted or unsubstituted $(C_3-C_6)$heteroalkyl combined with the nitrogen atom to which it is attached to form a four-, five-, six- or seven-membered ring optionally having additional substituents selected from substituted or unsubstituted $(C_1-C_8)$alkyl, substituted or unsubstituted $(C_1-C_8)$heteroalkyl and substituted or unsubstituted phenyl.

In another preferred embodiment, the substituted aryl groups are substituted phenyl groups.

In another preferred embodiment, one or both of $R^2$ and $R^3$ are selected from:

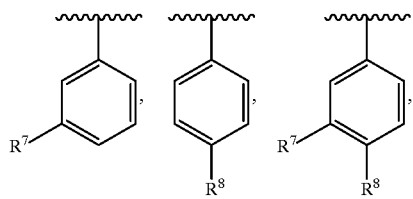

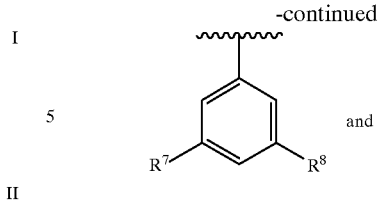

in which, $R^7$, $R^8$ and $R^9$ are independently selected from hydroxyl, halogen, nitro, cyano, substituted or unsubstituted $(C_1-C_6)$alkyl, $(C_1-C_6)$haloalkyl, substituted or unsubstituted $(C_1-C_6)$heteroalkyl, $(C_1-C_6)$alkoxy, $(C_1-C_6)$haloalkoxy, $(C_1-C_6)$alkylthio, substituted or unsubstituted aryl, substituted or unsubstituted heteroaryl, alkanoyl, alkoxycarbonyl, alkylcarbamoyl, sulfonyl, sulfamoyl and NR⁴R⁵, wherein $R^4$ and $R^5$ are defined as above.

In each of the above $R^7$, $R^8$ and $R^9$ groups, the alkyl portions of, for example, $(C_1-C_6)$alkyl, $(C_1-C_6)$alkylthio and $(C_1-C_6)$alkoxy may be further substituted with, for example, one or more halogen, hydroxy, nitro, cyano group, etc.

In a further preferred embodiment, $R^2$ and $R^3$ are independently selected from:

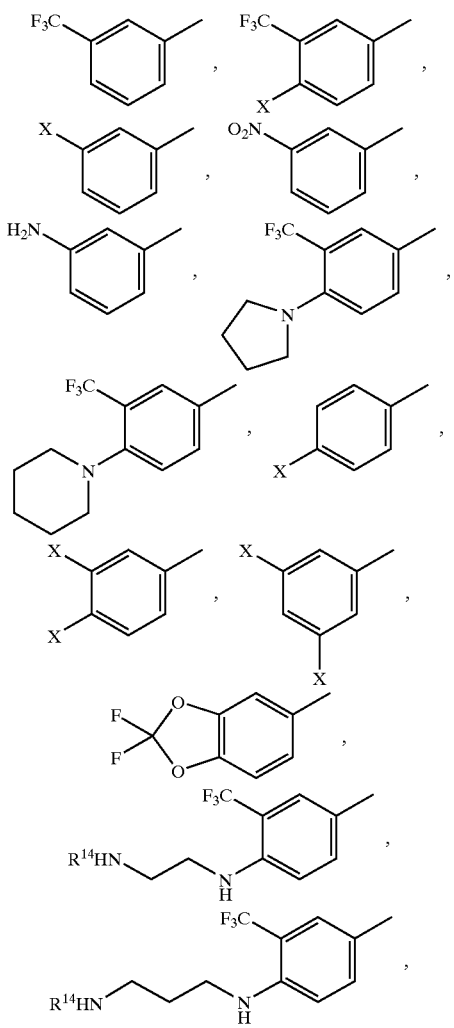

-continued

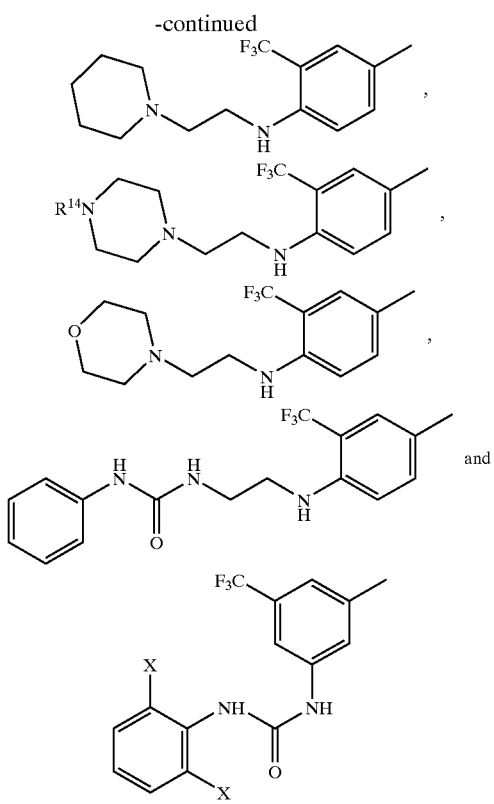

and wherein X is a halogen, preferably Cl or F, and $R^{14}$ is selected from hydrogen, substituted or unsubstituted $(C_1-C_8)$alkyl, $C(O)_mR^4$, $C(O)NR^4R^5$, $S(O)_nR^4$, $SO_2NR^4R^5$, $NR^4R^5$, $NR^6C(O)_mR^4$, $NR^6C(O)NR^4R^5$, $NR^6S(O)_nR^4$, $OC(O)_mR^4$ and $OC(O)NR^4R^5$. $R^4$, $R^5$, $R^6$ and m and n are defined as above.

In yet another preferred embodiment, the present invention provides compounds of formula (III):

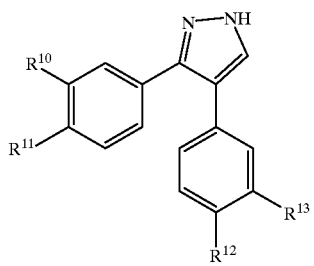

III in which, $R^{10}$, $R^{11}$, $R^{12}$ and $R^{13}$ are independently selected from H, halogen and haloalkyl groups, with the proviso that at least two of $R^{10}$, $R^{11}$, $R^{12}$ and $R^{13}$ are groups are other than H. In this embodiment, the preferred halogen groups are chloro and fluoro groups and particularly preferred distributions of the chloro and fluoro groups results in a first compound in which $R^{10}$, $R^{11}$ and $R^{13}$ are chloro or fluoro groups and a second compound in which $R^{10}$, $R^{12}$ and $R^{13}$ are chloro or fluoro groups.

In another preferred embodiment, the compounds of the invention have the formula (IV):

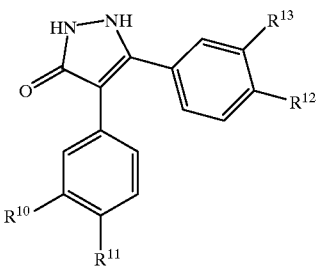

IV in which, $R^{10}$, $R^{11}$, $R^{12}$ and $R^{13}$ are independently selected from H, halogen and haloalkyl groups. In a still further preferred embodiment, $R^{11}$ and $R^{13}$ are H. In yet another preferred embodiment, $R^{10}$ is —$CF_3$ and $R^{12}$ is Cl or F.

In yet another preferred embodiment, the substituted heteroaryl groups contain one heteroatom selected from N, O and S.

In a further preferred embodiment, $R^2$ and $R^3$ are independently selected from:

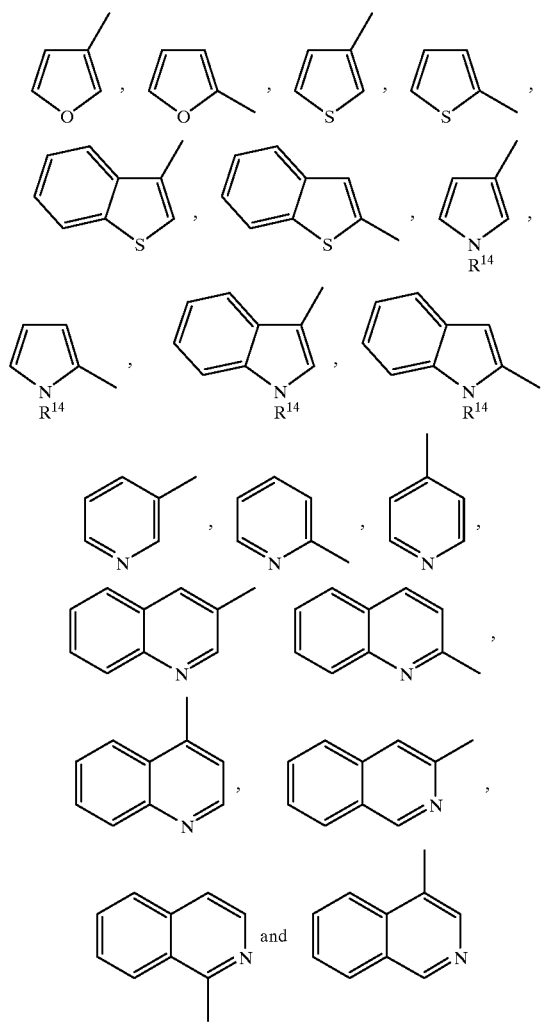

wherein $R^{14}$ is defined as above.

Synthesis of Pyrazoles and Related Derivatives

Compounds of the present invention can be prepared using readily available materials or known intermediates.

Schemes 1 and 2 provide exemplary synthetic routes for the production of selected compounds of the invention. One of skill in the art will understand that additional methods are also useful.

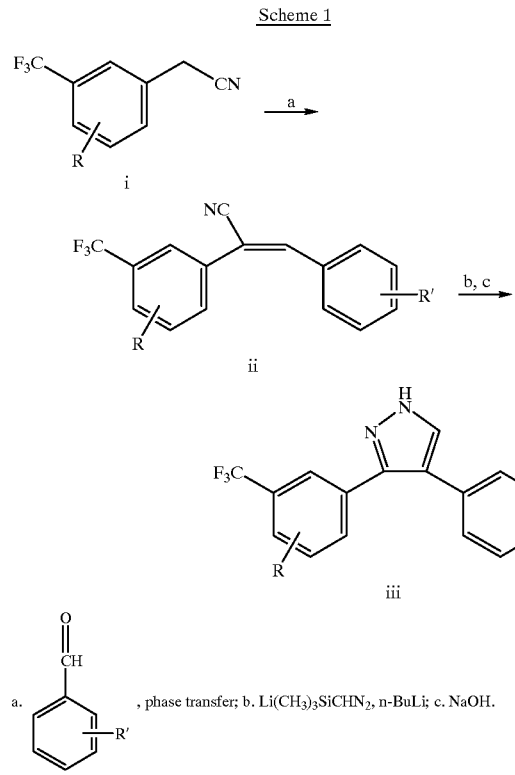

In Scheme 1, an aryl derivative (i) with an active hydrogen (e.g., arylacetonitrile) is condensed with an aryl aldehyde under phase transfer conditions to form the corresponding benzylidene (ii). The benzylidene derivative is subsequently reacted with an agent, such as lithium trimethylsilyldiazomethane to form the desired cyclized adduct, which is subjected to a basic reaction milieu to produce a substituted pyrazole (iii).

Scheme 2 provides an exemplary route to selected pyrazolone-based compounds of the invention.

In Scheme 2, an aryl derivative (iv) with an active hydrogen and a leaving group (e.g. ethyl ester) is deprotonated with a base, such as n-butyllithium, and coupled to an activated aryl carbonyl derivative, such as an acyl halide. The resulting substituted ketone (v) is reacted with a nitrogen donor, such as hydrazine in an acidic milieu, thereby forming a substituted pyrazolone (vi).

Regarding the molecular structures set forth in Schemes 1 and 2, one of skill in the art will readily appreciate that precursor and intermediates having substituents other than phenyl derivatives, e.g., heteroaryl derivatives such as thiophene derivatives, can be used to practice the synthetic route. Moreover, it will be appreciated that the groups R and R' indicate, in a very general sense, substituents on the aryl groups. R and R' can be the same or different. Both R and R' can represent a single substituent or multiple substituents. When R and/or R' represent multiple substituents, each R and R' can be the same or different.

Methods of Using the Compounds as Antimicrobial Agents

The compounds of invention are preferably inhibitors of RNA polymerase activity. In a preferred embodiment, the compounds of the invention have an $IC_{50}$ against a RNA polymerase of from about 0.1 $\mu$M to about 250 $\mu$M, more preferably from about 1 $\mu$M to about 100 $\mu$M. The $IC_{50}$ values of the compounds of the invention can be determined using art-recognized assays, such as that set forth in Example 39.

Still further preferred compounds inhibit the growth and reproduction of microorganisms (e.g., bacteria, viruses, mycobacterium, yeasts, and parasites). Thus, certain preferred compounds will interact with a microorganism with a minimum inhibitory concentration of from 1 nM to about 250 $\mu$M, more preferably from about 50 nM to about 100 $\mu$M, and even more preferably from about 1 $\mu$M to about 10 $\mu$M. The minimum inhibitory concentration (MIC) of the compounds of the invention can be determined using art-recognized assays, such as those set forth in Example 39.

The spectrum of inhibition of the compounds of the invention, i.e., the range of microorganisms whose growth and reproduction are inhibited by the compounds of the invention, may be narrow, broad or extended, as determined in a standard test system.

In another preferred embodiment, the compounds of the invention are used to modulate the growth of microorganisms on a surface. As used herein, a surface refers generally to a wide range of objects, including, for example, household, industrial and hospital surfaces (e.g., fixtures, floors, linens). Also included are surfaces, such as tissues (e.g., skin, mucosal), and organs (e.g., ocular). When the surface is a tissue or organ, the compounds of the invention, in this embodiment, will generally be administered topically and are useful when administered in vivo, in vitro and ex vivo.

In another preferred embodiment, the compounds of the invention are used to reduce, retard or prevent a microbial infection in a subject. In this embodiment, the subject is treated with an amount effective to reduce, retard or prevent the infection.

Evaluation of Compounds as Antimicrobial Agents

The compounds of the present invention can be evaluated for antimicrobial activity in a variety of assay formats known to those of skill in art. The specific assays used to select the most appropriate compound for use will typically depend on the targeted microorganism or infection.

One common assay involves evaluation of the compounds as RNA polymerase inhibitors. In this assay, buffer (250 mM KCl, 5% glycerol, 10 mM $MgCl_2$, 0.1 mg/ml BSA) is combined with 6 mM β-M.E., PT5 DNA template, and 1.3 $\mu$g/rxn Sigma$^{70}$ saturated $E.\ coli$ RNA Polymerase (Epicenter). The compound is then added in a manner not to exceed 5% DMSO. Nucleotide triphosphates are then added at the following concentration: 250 $\mu$M ATP, CTP and UTP with 100 $\mu$M cold CTP and 50 $\mu$M $\alpha$-$^{32}$P CTP. The mixture is incubated for 10 min at about 37° C. A [2×] loading buffer is added and the mixture is then run on a 6% urea denaturing PAGE until bromophenol blue reaches the edge of plate. The gel is soaked (about 20 minutes in 10% MeOH and 10% acetic acid, to remove urea), then dried (about 55 minutes at about 85° C. (BioRad Gel Drier)) and exposed to a Phospho Imaging Plate for 1 hour. The plate is then read on a Fujix Bas1000 Imaging System and quantified using MacBas v2.0 software. An $IC_{50}$ (in $\mu$M) can be calculated as the concentration of a drug which reduces the enzyme activity to 50% of the control.

For Minimum Inhibitory Concentration (MIC) determinations for selected bacteria, log phase growing bacteria are re-suspended at $1\times10^5$ bacteria per mL in LB medium. The compound is added and two-fold dilutions are made. The final volume in the 96-well plate is about 100 $\mu$L. The plate is incubated at 37° C. in the dark with shaking. After 16 hours of incubation, growth is monitored by reading A600 or by visual inspection. MIC is defined as the minimum concentration of drug resulting in inhibition of visible growth of bacterial under the conditions described (above) in National Committee for Clinical Laboratory Standards 1993. Methods for dilution antimicrobial susceptibility tests for bacteria that grow aerobically. Approved standard M7-A3; National Committee for Clinical Laboratory Standards: Villanova, Pa.

Formulations and Administration of Antimicrobial Agents

The compounds of the present invention can be prepared and administered in a wide variety of oral, topical and parenteral dosage forms. Thus, the compounds of the present invention can be administered by injection, that is, intravenously, intramuscularly, intracutaneously, subcutaneously, intraduodenally, or intraperitoneally. The present invention also contemplates the administration of the compounds of the present invention in a depot formulation. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of formula I, II or a pharmaceutically acceptable salt or prodrug thereof.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents.

In therapeutic use for the treatment of bacterial infections, the compounds utilized in the pharmaceutical method of the invention are administered at the initial dosage of about 0.001 mg/kg to about 100 mg/kg daily. A daily dose range of about 0.1 mg/kg to about 10 mg/kg is preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

In another preferred embodiment, the compounds and compositions of the invention are formulated to include or are used with other antimicrobial agents. In certain patient populations and with particular antimicrobial disorders, combination therapy results in increased efficacy over single-agent therapy. Combination therapy may also allow for the reduction in dosage of one or more of the agents used in combination therapy and, concomitantly, result in the reduction of adverse effects associated with each agent.

A wide range of antimicrobial agents can be used with the compounds, compositions and methods of the present invention. Such agents can be categorized based on their mechanism of action and/or their chemical structure or properties. For example, antimicrobial agents may act by interfering with cell wall synthesis, plasma membrane integrity, nucleic acid synthesis, ribosomal function, and folate synthesis. The compounds and compositions of the present invention may be used in conjunction with antimicrobial agents from each of these categories. In preferred embodiments, the compounds and compositions of the present invention are used in combination with antibiotics.

Agents that interfere with cell wall synthesis include the β-lactams (e.g, penicillins (including, for example, penicillin V, penicillin G, amoxicillin, ampicillin, nafcillin, ticarcillin, carbenicillin, and cloxacillin) and cephalosporins (including, for example, cephalexin, cefoxitin, ceforanide, and cefaclor)), which inhibit peptidoglycan polymerization, and by vancomycin, which combines with cell wall substrates. Agents with interfere with plasma membrane integrity, causing leakage, include, the polymyxins (including, for example, polymyxin B and colistin). The plasma membrane sterols of fungi are targeted by polyenes such as amphotericin. Agents which affect nucleic acid synthesis include the quinolones (for example, ciprofloxacin and norfloxacin) which bind to a bacterial complex of DNA and DNA gyrase, thereby blocking DNA replication, and rifampin-related agents that block RNA synthesis by binding to DNA directed RNA polymerase. Agents that interfere with ribosomal function include the aminoglycosides (e.g., gentamicin, tobramycin and neomycin), tetracycline, chloramphenicol, the macrolides (e.g., erythromycin and clarithormycin) and clindamycin. The sulfonamides (sulfamethoxazole and sulfisoxazole) and trimethoprim represent agents involved in blocking the synthesis of the folate needed for DNA replication. Other agents suitable for combination therapy include biosurfactants (e.g., circulin, EM49, polypeptin, brecistin, cerexin, tridecephin, surfactin, subsporin, mycosubtilisin, bacillomycin), and miscellaneous antibiotics (e.g., capreomycin, bacitracin, gramicidin, gramicidin S, tyrocidine).

The following examples are offered by way of illustration and are not intended to either define or limit the scope of the invention.

EXAMPLES

The Examples set forth herein below provide exemplary syntheses of certain representative compounds of the invention. Also provided are exemplary methods for assaying the compounds of the invention for their activity ($IC_{50}$) as inhibitors of RNA polymerase and assays for determining the minimum inhibitory concentration (MIC) of the compounds of the invention against microorganisms.

Materials and Methods

Reagents and solvents used below were obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz. Electron Ionization (EI) mass spectra were recorded on a Hewlett Packard 5989A mass spectrometer. Mass spectrometry results are reported as the ratio of mass over charge, followed by the relative abundance of each ion (in parentheses). In tables, a single m/e value is reported for the M+H (or as noted M–H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM $NH_4OAc$ in acetonitrile/water as delivery solvent.

Example 1

Example 1 sets forth the synthesis of a compound having a structure according to formula 1:

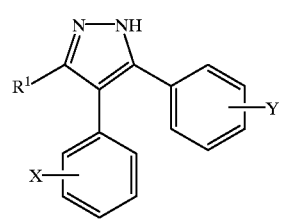

wherein $R^1$ is hydrogen, X is hydrogen and Y is 3-$CF_3$.

1.1 Synthesis of α-benzylidene-2-trifluoromethylphenylacetonitrile

To a stirred mixture of tetrabutylammonium iodide (300 mg, 0.81 mmol) and 1 N NaOH (12.15 mL, 12.15 mmol) in dichloromethane (20 mL) was added 3-trifluoromethylphenylacetonitrile (1.26 mL, 8.10 mmol) followed by benzylaldehyde (0.823 mL, 8.1 mmol) at r.t. After stirring at r.t. for 18 h, the reaction mixture was diluted with additional dichloromethane, and partitioned. The dichloromethane layer was washed with water twice, dried over $MgSO_4$, filtered and concentrated. The crude product was used directly in the next step, or purified by flash chromatography on silica gel with 10:1 hexanes/AcOEt as eluent to give pure product, 2.13 g, 96.3%.

1.2 Synthesis of Compound of Formula 1: $R^1$ is $SiMe_3$; X is H; Y is 3-$CF_3$ To a stirred solution of trimethylsilyldiazomethane (2 M in hexane, 1.32 mL, 2.64 mmol) in THF (13 mL) was added dropwise n-butyllithium (1.6 M, in hexane, 1.65 mL, 2.64 mmol) at −78° C. After an additional 20 min at −78° C., a solution of α-benzylidene-3-trifluoromethylphenylacetonitrile (0.60 g, 2.20 mmol) in THF (3 mL) was added. Stirring continued overnight while the temperature was allowed to rise to r.t. slowly. The reaction mixture was diluted with AcOEt, washed with 0.5 N aqueous HCl (2×) and brine (1×), dried over $MgSO_4$, filtered, and concentrated to give an oily product (738 mg).

1.3 Purification of 1.2

The crude product from 1.2, above, was treated with 10% KOH (1.80 mL, 3.56 mmol) in ethanol (15 mL) at 90° C. for 3 hr. After cooling to r.t., most of the ethanol was removed by rotary evaporation under reduced pressure. The residual material was taken up in AcOEt, washed with brine twice, dried over $MgSO_4$, filtered and concentrated to give an oil. The crude product was purified by flash chromatography on silica gel eluted with 2:1 hexanes/AcOEt to give 322 mg of pure product (50.9% for two steps).

$^1$H NMR ($CDCl_3$) δ 7.80 (s, 1H), 7.72 (s, 1H), 7.62 (d, J=7.8 Hz, 1H), 7.57 (d, J=7.7 Hz, 1H), 7.43 (t, J=7.3 Hz, 1H), 7.29 (m, 5H). MS (ES+): 289 (M+H), MS (ES−): 287 (M−H).

Example 2

Example 2 sets forth the synthesis of a compound having a structure according to formula 1, wherein $R^1$ is hydrogen, X is hydrogen and Y is 3—$OCH_3$.

The title compound was prepared in 15% yield according to method described in Example 1, with the exception that 3-methoxyphenylacetonitrile was substituted for 3-trifluoromethylphenylacetonitrile in Step 1.1.

$^1$H NMR ($CDCl_3$) δ 7.70 (s, 1H), 7.28 (m, 6H), 7.04 (d, J=7.6 Hz, 1H), 6.99 (s, 1H), 6.88 (d, J=7.2 Hz, 1H), 3.70 (s, 3H). MS (ES+): 251 (M+H), MS (ES−): 249 (M−H).

Example 3

Example 3 sets forth the synthesis of a compound having a structure according to formula 1, wherein $R^1$ is hydrogen, X is hydrogen, and Y is 4-Cl.

The title compound was prepared in 8% yield according to method described for Example 1, with the exception that 4-chlorophenylacetonitrile was substituted for 3-trifluoromethylphenylacetonitrile in Step 1.1.

$^1$H NMR ($CDCl_3$) δ 7.70 (s, 1H), 7.40 (d, J=8.6 Hz, 2H), 7.30 (m, 8H). MS (ES+): 255 (M+H), MS (ES−): 253 (M−H). Anal. Calcd. for $C_{15}H_{11}ClN_2$: C, 70.73; H, 4.35; N, 11.00. Found: C, 70.59; H, 4.62; N, 10.23.

Example 4

Example 4 sets forth the synthesis of a compound of formula 1, wherein $R^1$ is hydrogen, X is hydrogen and Y is 3,4-di-Cl.

The title compound was prepared in 15% yield according to the method described in Example 1, with the exception that 3,4-dichlorophenylacetonitrile was substituted for 3-trifluoromethylphenylacetonitrile in Step 1.1.

$^1$H NMR (DMSO) δ 13.24 (s, 1H), 7.99 (s, 1H), 7.06 (m, 2H), 7.35 (m, 3H), 7.28 (m, 3H). MS (ES+): 289 (M+H), MS (ES−): 287 (M−H).

Example 5

Example 5 sets forth the synthesis of a compound of formula 1, wherein $R^1$ is hydrogen, X is hydrogen and Y is 4-$CH_3$.

The title compound was prepared in 15% yield according to the method described in Example 1, with the exception that 4-methylphenylacetonitrile was substituted for 3-trifluoromethylphenylacetonitrile in Step 1.1.

$^1$H NMR ($CDCl_3$) δ 7.70 (s, 1H), 7.29 (m, 6H), 7.16 (d, J=8 Hz, 2H). MS (ES+): 235 (M+H), MS (ES−): 233 (M−H). Anal. Calcd. for $C_{16}H_{14}N_2$: C, 82.02; H, 6.02; N, 11.96. Found: C, 80.79; H, 6.03; N, 11.93.

Example 6

Example 6 sets forth the synthesis of a compound of formula 1, wherein $R^1$ is hydrogen, X is hydrogen and Y is 4-$OCH_3$.

The title compound was prepared in 13% yield according to the method described in Example 1, with the exception that 4-methoxyphenylacetonitrile was substituted for 3-trifluoromethylphenylacetonitrile in Step 1.1.

$^1$H NMR ($CDCl_3$) δ 7.70 (s, 1H), 7.37 (d, J=8.7 Hz, 2H), 7.31 (m, 4H), 7.26 (s, 1H), 6.88 (d, J=8.8 Hz, 2H), 3.82 (s, 3H). MS (ES+): 251 (M+H), MS (ES−): 249 (M−H). Anal. Calcd. for $C_{16}H_{14}N_2O$: C, 76.78; H, 5.64; N, 11.19. Found: C, 76.48; H, 5.92; N, 10.99.

Example 7

Example 7 sets forth the synthesis of a compound of formula 1, wherein $R^1$ is hydrogen, X is 3-Cl and Y is 3,4-di-Cl.

The title compound was prepared in 3% yield according to the method described in Example 1, with the exception that 3,4-dichlorophenylacetonitrile was substituted for 3-trifluoromethylphenylacetonitrile and 3-chlorobenzaldehyde was substituted for benzaldehyde in Step 1.1.

$^1$H NMR ($CDCl_3$) δ 10.53 (bs, 1H), 7.70 (s, 1H), 7.39 (d, J=8.0 Hz, 1H), 7.31(s, 1H), 7.25(m, 3H), 7.12 (d, J=8.0 Hz, 1H). MS (ES+): (M+H), MS (ES−): (M−H). Anal. Calcd. for $C_{15}H_9Cl_3N_2$: C, 55.67; H, 2.80; N, 8.66. Found: C, 56.79; H, 3.13; N, 8.53.

Example 8

Example 8 sets forth the synthesis of a compound of formula 1, in which R1 is H, X is 3,4-di-Cl, and Y is 3-Cl.

The title compound was prepared in 25% yield according to the method described in Example 1, with the exception that 3-chlorophenylacetonitrile was substituted for 3-trifluoromethylphenylacetonitrile and 3,4-dichlorobenzaldehyde was substituted for benzaldehyde in Step 1.1.

$^1$H NMR ($CDCl_3$) δ 7.72 (bs, 1H), 7.50 (s, 1H), 7.39 (m, 3H), 7.28 (m, 3H), 7.07 (d, J=8.3 Hz, 1H). MS (ES+): (M+H), MS (ES−): (M−H). Anal. Calcd. for $C_{15}H_9Cl_3N_2$: C, 55.67; H, 2.80; N, 8.66. Found: C, 55.58; H, 2.81; N, 8.55.

Example 9

Example 9 sets forth the synthesis of a compound of formula 1, wherein $R^1$ is H, X is 3-$CF_3$, 4-Cl, and Y is 3-Cl.

The title compound was prepared in 29% yield according to the method recited in Example 1, with the exception that 3-chlorophenylacetonitrile was substituted for 3-trifluoromethylphenylacetonitrile and 3-trifluoromethyl-4-chlorobenzaldehyde was substituted for benzaldehyde in Step 1.1.

$^1$H NMR ($CDCl_3$) δ 7.79 (bs, 1H), 7.63 (s, 1H), 7.49 (s, 1H), 7.43 (d, J=9.0 Hz, 1H), 7.32(m, 3H). MS (ES+): 357

(M+H), MS (ES−): 355 (M−H). Anal. Calcd. for $C_{16}H_9Cl_2F_3N_2$: C, 53.81; H, 2.54; N, 7.84. Found: C, 53.94; H, 2.56; N, 7.94.

Example 10

Example 10 sets forth the synthesis of a compound of formula 1, wherein R1 is H, X is 3-$CF_3$, 4-Cl, and Y is H.

The title compound was prepared in 16% yield according to method set forth in Example 1, with the exception that phenylacetonitrile was substituted for 3-trifluoromethylphenylacetonitrile and 3-trifluoromethyl-4-chlorobenzaldehyde was substituted for benzaldehyde in Step 1.1.

$^1$H NMR (CDCl$_3$) δ 7.74 (bs, 1H), 7.64 (s, 1H), 7.40 (m, 6H), 7.34 (d, J=8.1 Hz, 1H). MS (ES+): 323 (M+H), MS (ES−): 321 (M−H).

Example 11

Example 11 sets forth the synthesis of a compound of formula 1, wherein R1 is H, X is 3-$CF_3$, 4-F, and Y is 3-Cl.

The title compound was prepared in 16% yield according to method described for Example 1, with the exception that 3-chlorophenylacetonitrile was substituted for 3-trifluoromethylphenylacetonitrile and 3-trifluoromethyl-4-fluorobenzaldehyde was substituted for benzaldehyde in Step 1.1.

$^1$H NMR (CDCl$_3$) δ 7.73 (bs, 1H), 7.55 (dd, J=6.6, 2.2 Hz, 1H), 7.48 (t, J=1.6 Hz, 1H), Anal. Calcd. for $C_{16}H_9ClF_4N_2$: C, 56.40; H, 2.66; N 8.22. Found C, 56.44 H, 2.58; N 8.27.

Example 12

Example 12 sets forth the synthesis of a compound of formula 1, wherein R1 is H, X is 3-$CF_3$, 4-pyrrolin-1-yl, and Y is 3-Cl.

The title compounds was prepared in 85% yield by heating a sample of the compound from Example 11 with pyrrolidine (5 equiv.) in DMSO at 80° C. for 4 hr followed by aqueous work-up and chromatographic purification.

$^1$H NMR (CDCl$_3$) δ 7.69 (bs, 1H), 7.53 (s, 1H), 7.30 (m, 4H), 7.22 (d, J=8.7 Hz, 1H), 6.89 (d, J=8.8 Hz, 1H), 3.36 (m, 4H), 1.96 (m, 4H). MS (ES+): 392 (M+H), MS (ES−): 390 (M−H).

Example 13

Example 13 sets forth the synthesis of a compound having a structure according to formula 13:

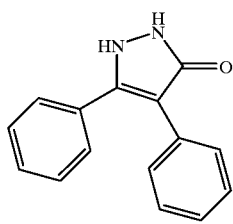

13

13.1 Synthesis of 3-oxo-2,3-diphenylpropionic acid ethyl ester

To 2.5 mL (0.033 mol) of diisopropylamine dissolved in 50 mL of anhydrous tetrahydrofuran at 0° C. under argon was added dropwise 11.1 mL (0.028 mol) of a 2.5 M solution of n-butyllithium in hexanes over 30 min. After the mixture was stirred at 0° C. for 20 min and cooled to −78° C., 2 mL (0.0126 mol) of ethyl phenylacetate was added followed by stirring for 30 min. The resulting solution was treated with 1.61 mL (0.014 mol) of benzoyl chloride at −78° C. After being stirred at −78° C. for 1 h, the reaction mixture was added to 10 mL of saturated NH$_4$Cl solution. The mixture was then diluted with ethyl acetate and washed with saturated NH$_4$Cl solution. The aqueous layer was extracted with ethyl acetate, and the combined organic layers were washed with water (1×) and then with saturated aqueous sodium chloride solution (1×). The organic layer was dried over anhydrous magnesium sulfate, filtered, and concentrated in vacuo. The residue was chromatographed on silica gel and eluted with 5-10% ethyl acetate/hexanes to give 1.2 g (36%) of 3-oxo-2,3-diphenylpropionic acid ethyl ester.

13.2 Synthesis of 4,5-diphenyl-1,2-dihydropyrazol-3-one

To 20 mL of an ethanol solution of 1.2 g (4.47mmol) of 3-oxo-2,3-diphenylpropionic acid ethyl ester was added 1.04 g (4.47 mmol) of camphoric acid and 140 μL (4.47 mmol) of hydrazine. After the mixture was refluxed for 20 min, the solvent was removed in vacuo, and the residue was triturated with 40% ethyl acetate/hexane (2 mL) three times to afford 343 mg of 4,5-diphenyl-1,2-dihydropyrazol-3-one in 27% yield.

$^1$H NMR (CDCl$_3$) δ 7.42 (dd, J1=8.4 Hz, J2=1.2 Hz, 1H), 7.38 (m, 5H), 7.32 (t, J=7.8 Hz, 2H), 7.23 (t, J=7.8 Hz, 1H). MS (ES+): 237 (M+H, 100).

Example 14

Example 14 sets forth the synthesis of a compound having a structure according to formula 14:

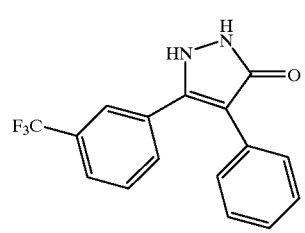

14

Following the procedures described in Example 13.1, with the exception that 3-trifluoromethyl benzoyl chloride was substituted for benzoyl chloride, 4-phenyl-5-(3-trifluoromethylphenyl)-1,2-dihydropyrazol-3-one was obtained, 275 mg, 25% yield.

$^1$H NMR (CDCl$_3$) δ 7.63 (s, 1H), 7.61 (d, J=7.7 Hz, 1H), 7.50 (d, J=7.7 Hz, 1H), 7.44 (t, J=7.7 Hz, 1H), 7.34 (t, J=7.7 Hz, 3H), 7.29 (d, J=7.6 Hz, 2H), 7.24 (tt, J1=7.2 Hz, J2=1.2 Hz, 1H). MS (ES+): 305 (M+H, 100).

Example 15

Example 15 sets forth the synthesis of a compound having a structure according to formula 15:

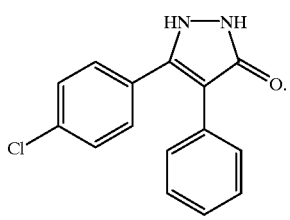

15

Following the procedures described in Example 13.1, with the exception that 4-chlorobenzoyl chloride was substituted for benzoyl chloride, 5-(4-chlorophenyl)-4-phenyl-1,2-dihydropyrazol-3-one was obtained, 275 mg, 38% yield.

$^1$H NMR (CDCl$_3$) δ 7.38 (m, 5H), 7.29 (d, J=8.0 Hz, 2H), 7.22 (d, J=8.0 Hz, 2H). MS (ES+): 271 (M+H, 100).

Example 16

Example 16 sets forth the synthesis of a compound having a structure according to formula 16:

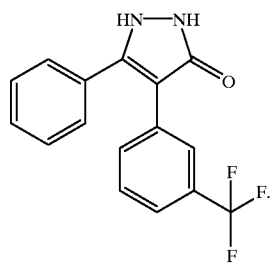

16

Following the procedures described in Example 13.1, with the exception that ethyl 3-(trifluoromethyl) phenylacetate is substituted for ethyl phenylacetate, 5-phenyl-4-(3-trifluoromethylphenyl)-1,2-dihydropyrazol-3-one was obtained, 340 mg, 17% yield.

$^1$H NMR (DMSO) δ 7.62 (s, 1H), 7.54 (d, J=8.0 Hz, 1H), 7.45 (d, J=7.7 Hz, 1H), 7.44 (s, 1H), 7.42 (t, J=7.7 Hz, 1H), 7.39 (m, 5H). MS (ES+): 305 (M+H, 100).

Example 17

Example 17 sets forth the synthesis of a compound having a structure according to formula 17:

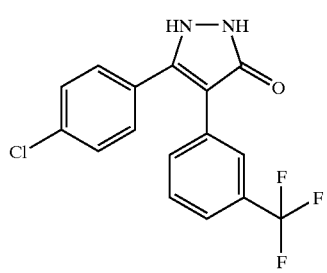

17

Following the procedures described in Example 16, with the exception that 4-chlorobenzoyl chloride is substituted for benzoyl chloride, 5-(4-chlorophenyl)-4-(3-trifluoromethylphenyl)-1,2-dihydropyrazol-3-one was obtained, 74 mg, 25% yield.

$^1$H NMR (CDCl$_3$) δ 7.68 (s, 1H), 7.45 (d, J=8.0 Hz, 1H), 7.43 (d, J=7.7 Hz, 1H), 7.36 (t, J=7.7 Hz, 1H), 7.29 (d, J=8.0 Hz, 2H), 7.22 (d, J=8.0 Hz, 2 H). MS (ES+): 339 (M+H, 100).

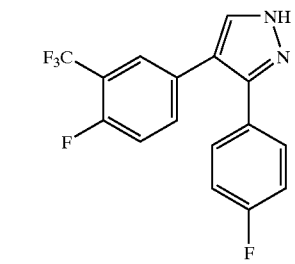

Example 18

Example 18 sets forth the synthesis of a compound having a structure according to formula 1, in which R$^1$ is H, X is 3-CF$_3$, 4-F, and Y is 4-F.

The title compound was prepared according to the method recited in Example 1, with the exception that 4-fluorophenylacetonitrile was substituted for 3-trifluoromethylphenylacetonitrile and 3-trifluoromethyl-4-fluorobenzaldehyde was substituted for benzaldehyde in Step 1.1.

$^1$H NMR (CDCl$_3$) δ 7.72 (s, 1H), 7.54 (dd, J$_a$=6.6 Hz, J$_b$=2.2 Hz, 1H), 7.40 (m, 3 H), 7.15 (t, J=9.5 Hz, 1H), 7.09 (t, J=8.6 Hz, 1H). MS (ES+): 325 (M+H), MS (ES−): 323 (M−H).

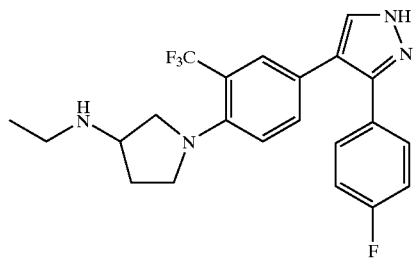

Example 19

Example 19 sets forth the synthesis of a compound having a structure according to formula 1, in which R$^1$ is H, X is 3-CF$_3$, 4-(3-ethylamino)pyrrolidin-1-yl, and Y is 4-F.

The title compounds was prepared in 85% yield by heating a sample of the compound from Example 18 with 3-ethylaminopyrrolidine (5 equiv.) in DMSO at 80° C. for 4 hr followed by aqueous work-up and chromatographic purification.

1H NMR (CDCl$_3$) δ 0.63 (s, 1H), 7.51 (d, J=2.2 Hz, 1H), 7.41 (td, J$_a$=5.4 Hz, J$_b$=3.5 Hz, 2H), 7.21 (dd, J$_a$=8.7 Hz, J$_b$=2.1 Hz, 1H), 7.04 (t, J=8.7 Hz, (2H), 6.9 (d, J=8.7 Hz, 1H), 3.46 (m, 3H), 3.34 (m, 1H), 3.21 (m, 1H), 2.74 Hz, (m, 2H), 2.22 (m, 1H), 1.88 (m, 1H), 1.18 (t, J=7.2 Hz, 3H). MS (ES+): 419 (M+H), MS (ES−): 417 (M−H).

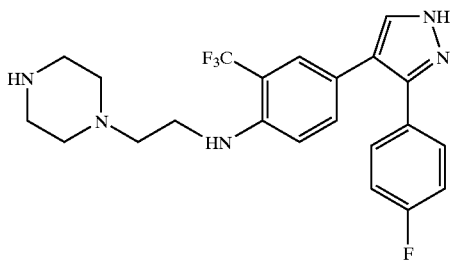

Example 20

Example 20 sets forth the synthesis of a compound having a structure according to formula 1, in which R¹ is H, X is 3-CF₃, 4-(2-piperazino)ethylamino, and Y is 4-F.

The title compound was prepared according to method described for Example 19, with the exception that 1-(2-aminoethyl)piperazine was substituted for 3-ethylaminopyrrolidine.

1H NMR (CDCl₃) δ 7.64 (s, 1H), 7.44 (td, $J_a$=6.0 Hz, $J_b$=2.7 Hz, 2H), 7.38 (d, J=1.9 Hz, 1H), 7.22 (dd, $J_a$=8.7 Hz, $J_b$=2.1 Hz, 1H), 7.04 (t, J=8.8 Hz, 2H), 6.63 (d, J=8.4 Hz, 1H), 5.38 (bs, 1H), 3.18 (q, J=4.8 Hz, 2H), 2.93 (t, J=4.9 Hz, 5H), 2.68 (t, J=6.0 Hz, 2H), 2.50 (bs, 4H). MS (ES−): 432 (M−H).

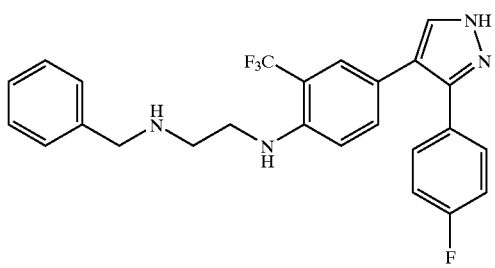

Example 21

Example 21 sets forth the synthesis of a compound having a structure according to formula 1, in which R¹ is H, X is 3-CF₃, 4-(2-benzylamino)ethylamino, and Y is 4-F.

The title compound was prepared according to method described for Example 19, with the exception that 2-benzylaminoethaylamine was substituted for 3-ethylaminopyrrolidine.

¹H NMR (CDCl₃) δ 7.64 (s, 1H), 7.41 (m, 2H), 7.33 (m, J=2.8 Hz, 3H), 7.27 (m, 2H), 7.21 (d, J=8.7 Hz, 2H), 7.04 (t, J=8.7 Hz, 2H), 6.64 (d. J=8.7 Hz, 1H), 5.08 (bs, 1H), 3.85 (s, 2H), 3.27 (q, J=5.6 Hz, 2H), 2.96 (t, J=5.7 Hz, 2H). MS (ES+):455 (M+H), MS (ES−): 453 (M−H).

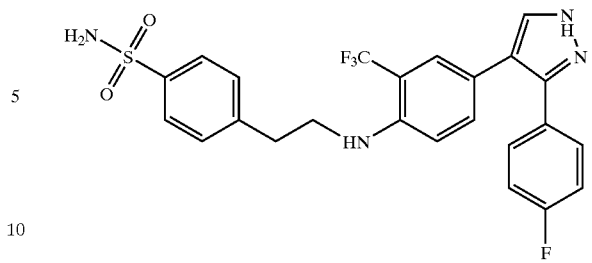

Example 22

Example 22 sets forth the synthesis of a compound having a structure according to formula 1, wherein R¹ is H, X is 3-CF₃, 4-[2-(4-sulfamoylphenyl)]ethylamino and Y is 4-F.

The title compound was prepared according to method described for Example 19, with the exception that 4-(2-aminoethyl)benzenesulfonamide was substituted for 3-ethylaminopyrrolidine.

¹H NMR (CDCl3) δ 7.89 (d, J=8.3 Hz, 2H), 7.66 (s, 1H), 7.45 (q, J=4.0 Hz, 2H), 7.37 (m, 3H), 7.21 (s, 1H), 7.05 (t, J=8.7 Hz, 2H), 6.70 (d, J=8.7 Hz, 1H), 4.81 (bs, 2H), 3.48 (t, J=6.8 Hz, 2H), 3.03(t, J=6.8 Hz, 2H), 2.98 (s, 1H). MS (ES+): 505 (M+H), MS (ES−): 503 (M−H).

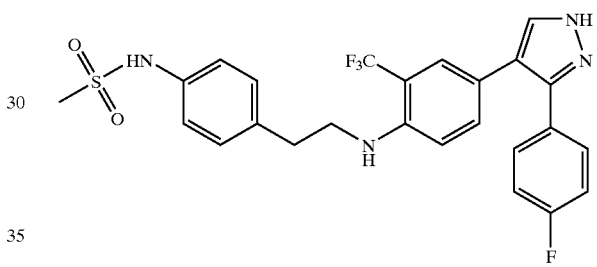

Example 23

Example 23 sets forth the synthesis of a compound having a structure according to formula 1, wherein R¹ is H, X is 3-CF₃, 4-[2-(4-(methanesulfonimidophenyl)]ethylamino and Y is 4-F.

The title compound was prepared according to method described for Example 19, with the exception that 2-[4-(methanesulfonamido)-phenyl]ethylamine was substituted for 3-ethylaminopyrrolidine.

¹H NMR (CDCl₃) δ 8.04 (s, 1H), 7.50 (q, $J_a$=8.8 Hz, $J_b$=5.4 Hz, 2H), 7.34 (s, 1H), 7.20 (m, 5H), 7.03 (t, J=8.8 Hz, 2H), 6.70 (d, J=8.6 Hz, 1H), 6.50 (S, 1H), 3.43 (m, 4H), 2.83 (s, 1H). MS (ES−): 517 (M−H).

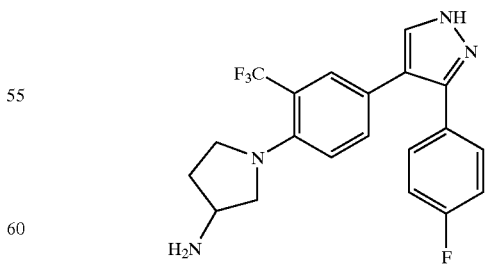

Example 24

Example 24 sets forth the synthesis of a compound having a structure according to formula 1, in which R¹ is H, X is 3-CF₃, 4-3-aminopyrrolidin-1-yl, and Y is 4-F.

The title compound was prepared according to method described for Example 19, with the exception that 3-aminopyrrolidine was substituted for 3-ethylaminopyrrolidine.

¹H NMR (CDCl₃) δ 7.57 (s, 1H), 7.50 (s, 1H), 7.41–7.37 (m, 2H), 7.20 (d, J=8.7 Hz, 1H), 6.99 (t, J=8.7 Hz, 2H), 6.86 (d, J=8.5 Hz, 1H), 3.65 (m, 1H), 3.50 (m, 2H), 3.30 (m, 1H), 3.06 (m,1H), 2.20 (m, 1H), 1.75 (m, 1H). MS (ES+): 391 M+H, MS (ES−): 389 (M−H).

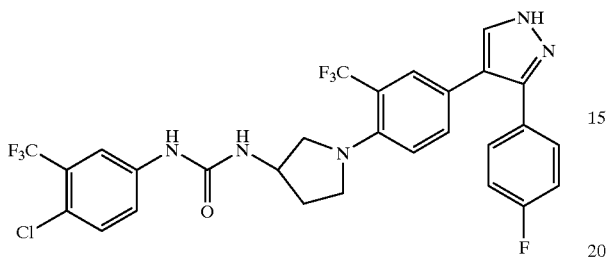

Example 25

Example 25 sets forth the synthesis of a compound having a structure according to formula 1, wherein $R^1$ is H, X is 3-CF3, 4-[3-(4-chloro-3-trifluoromethylphenylureido)]pyrrolidin-1-yl and Y is 4-F.

The title compound was prepared by reacting a sample of the compound from Example 24 with 3-chloro-4-trifluoromethylphenyl isocyanate (1 equiv.) in dichloromethane at r.t. until completion of reaction followed by aqueous washings with water and brine and chromatographic purification.

¹H NMR (DMSO) δ 13.02 (bs, 1H), 8.88 (s, 1H), 8.06 (s, 1H), 7.54 (s, 2H), 7.45–7.42 (m, 3H), 7.35 (d, J=8.8 Hz, 1H), 7.21 (bs, 2H), 7.08 (d, J=8.8 Hz, 1H), 6.65 (d, J=6.9 Hz, 1H), 4.28 (m, 1H), 3.52 (m, 1H), 3.41 (m, 1H), 3.13 (m, 1H), 2.20 (m, 1H), 1.88 (t, J=6.4 Hz, 1H). MS (ES+): 612 (M+H).

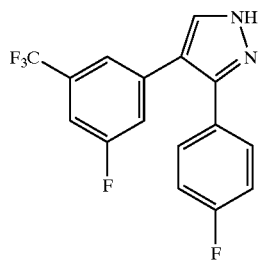

Example 26

Example 26 sets forth the synthesis of a compound having a structure according to formula 1, in which $R^1$ is H, X is 3-CF₃, 5-F, and Y is 4-F.

The title compound was prepared according to the method recited in Example 1, with the exception that 4-fluorophenylacetonitrile was substituted for 3-trifluoromethylphenylacetonitrile and 3-trifluoromethyl-5-fluorobenzaldehyde was substituted for benzaldehyde in Step 1.1.

¹H NMR (CDCl₃) δ 7.42 (s, 1H), 7.40 (m, 2H), 7.34 (s, 1H), 7.21 (d, J=2.2 Hz, 1H), 7.10 (m, 3H). MS (ES−): 323 (M−H).

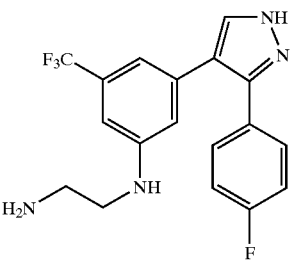

Example 27

Example 27 sets forth the synthesis of a compound having a structure according to formula 1, in which $R^1$ is H, X is 3-CF₃, 5-(2-amino)ethylamino, and Y is 4-F.

The title compound was prepared by reacting a sample of the compound from Example 26 with ethylenediamine (5 equiv.) in DMSO at 110° C. until completion of reaction followed by aqueous washings with water and brine and chromatographic purification. ¹H NMR (CDCl₃) δ 7.68 (s, 1H), 7.43 (dd, J=16, 6.8 Hz, 2H), 7.05 (dd, J=8.4, 8.2 Hz, 2H), 6.85 (s, 1H), 6.71 (s, 1H), 6.58 (s, 1H), 4.30 (s, 1H), 3.10 (q, J=5.8 Hz, 2H), 2.90 (q, J=5.8 Hz, 2H). MS (ES+): 365 (M+H), MS (ES−): 3363 (M−H).

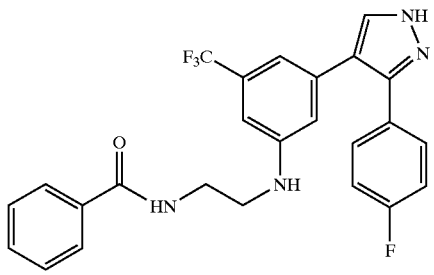

Example 28

Example 28 sets forth the synthesis of a compound having a structure according to formula 1, in which $R^1$ is H, X is 3-CF₃, 5-(2-phenylacetomidoethyl)amino, and Y is 4-F.

The title compound was obtained by treating a sample of the compound from Example 27 with benzoyl chloride (1.0 equiv.) and triethylamine (1.0 equiv.) at 0° C. for 30 min followed by aqueous washings with water and brine and chromatographic purification.

¹H NMR (CDCl₃) δ 7.73 (d, J=8.3 Hz, 3H), 7.51 (m, J=7.3 Hz, 1H), 7.43 (t, J=7.8 Hz, 4H), 7.04 (t, J=8.7 Hz, 2H), 6.85 (s, 1H), 6.72 (s, 1H), 6.64 (s, 1H), 6.40 (bs, 1H), 3.67 (q, J=5.8 Hz, 2H), 3.31 (t, J=5.7 Hz, 2H). MS (ES+): 469 (M+H), MS (ES−): 467 (M−H).

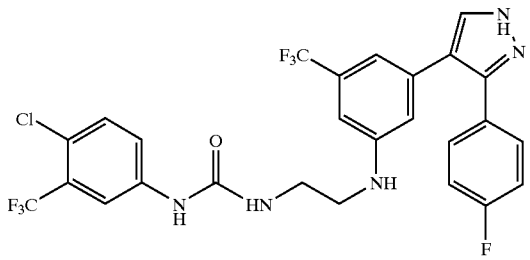

Example 29

Example 29 sets forth the synthesis of a compound having a structure according to formula 1, in which $R^1$ is H, X is 3-CF$_3$, 5-[2-(4-chloro-3-trifluoromethylphenylureido)]ethylamino and Y is 4-F.

The title compound was prepared by reacting a sample of the compound from Example 27 with 3-chloro-4-trifluoromethylphenyl isocyanate (1 equiv.) in dichloromethane at r.t. until the completion of reaction followed by aqueous washings with water and brine and chromatographic purification.

$^1$H NMR (DMSO) δ 13.05 (bs, 1H), 9.07 (s, 1H), 8.05 (s, 1H), 7.55 (m, J=8.8 Hz, 2H), 7.45 (m, 2H), 7.10 (bs, 1H), 6.74 (s, 2H), 6.64 (s, 1H), 6.38 (m, J=5.5 Hz, 1H), 6.21 (m, 1H), 3.19 (m, 2H), 3.10 (m, 2H). MS (ES+): 586 (M+H).

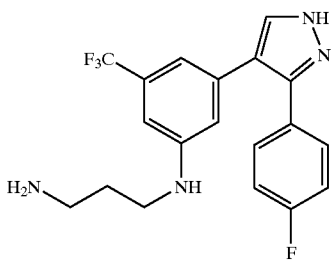

Example 30

Example 30 sets forth the synthesis of a compound having a structure according to formula 1, in which $R^1$ is H, X is 3-CF$_3$, 5-3-aminopropylamino and Y is 4-F.

The title compound was prepared by reacting a sample of the compound from Example 26 with propyl-1,3-diamine (5 equiv.) in DMSO at 110° C. until the completion of reaction followed by aqueous washings with water and brine and chromatographic purification.

$^1$H NMR (CDCl$_3$) δ 7.69 (s, 1H), 7.44 (dd, J$_a$=8.8 Hz, J$_b$=3.6 Hz, 2H), 7.05 (t, J=8.7 Hz, 2H), 6.84 (s, 1H), 6.69 (s, 1H), 6.58 (s, 1H), 3.12 (t, J=6.7 Hz, 2H), 2.82 (t, J=6.6 Hz, 2H), 1.70 (m, J=6.6 Hz, 2H). MS (ES+): 379 (M+H), MS (ES−): 377 (M−H).

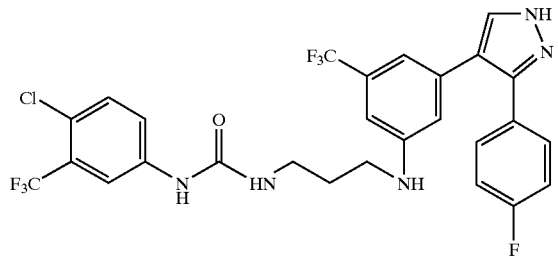

Example 31

Example 31 sets forth the synthesis of a compound having a structure according to formula 1, in which $R^1$ is H, X is 3-CF$_3$, 5-[3-(4-chloro-3-trifluoromethylphenylureido)]propylamino, and Y is 4-F.

The title compound was prepared by reacting a sample of the compound from Example 30 with 3-chloro-4-trifluoromethylphenyl isocyanate (1 equiv.) in dichloromethane at r.t. until the completion of reaction followed by aqueous washings with water and brine and chromatographic purification.

$^1$H NMR (CDCl$_3$) δ 7.69 (s, 1H), 7.60 (d, J=2.6 Hz, 1H), 7.49 (dd, J$_a$=8.7 J$_b$=2.6 Hz, 1H), 7.42 (dd, J$_a$=8.9 Hz, J$_b$=3.3 Hz, 2H), 7.37 (d, J=9.0 Hz, 1H), 7.04 (t, J=8.6 Hz, 2H), 6.87 (s, 1H), 6.71 (s,1H), 6.60 (d, J=17.3 Hz, 2H), 4.79 (bs, 1H), 3.34 (t, J=6.2 Hz, 2H), 3.12 (t, J=6.4 Hz, 2H), 1.71 (m, J=6.3 Hz, 2H MS (ES): 598 (M−H).

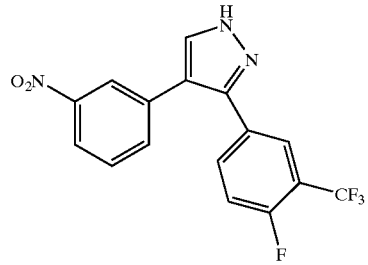

Example 32

Example 32 sets forth the synthesis of a compound having a structure according to formula 1, in which $R^1$ is H, X is 3-NO$_2$, and Y is 3-CF$_3$, 4-F,.

The title compound was prepared according to the method recited in Example 1, with the exception that 4-fluoro-3-trifluoromethylphenylacetonitrile was substituted for 3-trifluoromethylphenylacetonitrile and 3-nitrobenzaldehyde was substituted for benzaldehyde in Step 1.1.

$^1$H NMR (DMSO) δ 8.28 (s, 1H), 8.13–8.10 (m, 2H), 7.77–7.70 (m, 3H), 7.63 (t, J=7.9 Hz, 1H), 7.52 (t, J=9.4 Hz, 1H). MS (ES+): 352 (M+H).

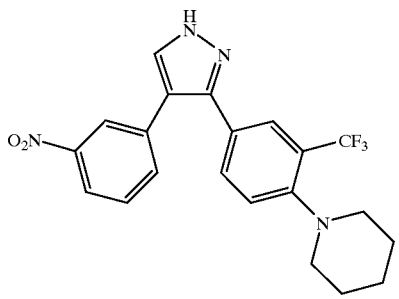

Example 33

Example 33 sets forth the synthesis of a compound having a structure according to formula 1, in which $R^1$ is H, X is 3-NO$_2$, and Y is 3-CF$_3$, 4-piperidin-1-yl.

The title compound was prepared by reacting a sample of the compound from Example 32 with piperidine (5 equiv.) in DMSO at 110°C. until the completion of reaction followed by aqueous washings with water and brine and chromatographic purification.

$^1$H NMR (DMSO) δ 8.24 (bs, 1H), 8.10 (d, J=8.1 Hz, 1H), 8.07 (s, 1H), 7.74 (d, J=7.8 Hz, 1H), 7.67–7.61 (m, 3H), 7.48 (d, J=8.8 Hz, 1H), 2.82 (M, 4H), 1.63 (s, 4H), 1.53 (m, 2H). MS (ES+): 417 (M+H).

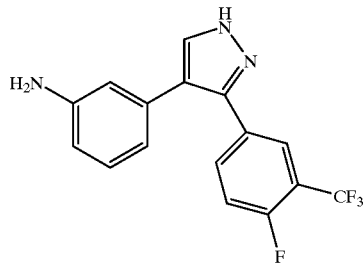

Example 34

Example 34 sets forth the synthesis of a compound having a structure according to formula 1, in which $R^1$ is H, X is 3-NH$_2$ and Y is 3-CF$_3$, 4-F.

The title compound was prepared by treating a sample of the compound from Example 32 with SnCl$_2$.H$_2$O (3 equiv.) in refluxing AcOEt until completion of reaction followed by aqueous work-up and chromatographic purification.

$^1$H NMR (DMSO) δ 7.86 (s, 1H), 7.78 (m, 2H), 7.48 (bs, 1H), 6.98 (t, J=8.0 Hz, 1H), 6.48 (s, 2H), 7.52 (t, J=7.5 Hz, 1H), 5.05 (s, 2H). MS (ES+): 322 (M+H).

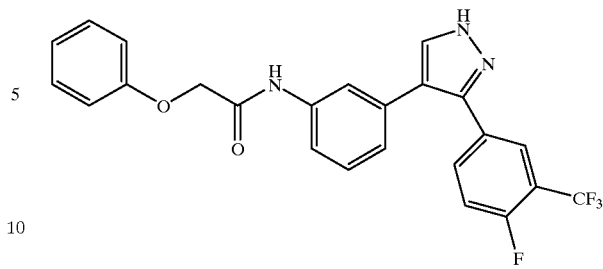

Example 35

Example 35 sets forth the synthesis of a compound having a structure according to formula 1, in which $R^1$ is H, X is 3-phenoxyacetomido, and Y is 4-F, 3-CF$_3$.

The title compound was prepared by treating a sample of the compound from Example 34 with phenoxyacetyl chloride (1 equiv.) and triethylamine (1 equiv.) in AcOEt at r.t. until the completion of reaction followed by aqueous washings with water and brine and chromatographic purification.

$^1$H NMR (DMSO) δ 10.06 (s, 1H), 7.98 (bs, 1H), 7.77–7.75 (m, 2H), 7.59 (d, J=6.6 Hz, 2H), 7.48 (s, 1H), 7.30 (t, J=8.0 Hz, 3H), 6.98 (d, J=7.0 Hz, 4H), 4.66 (s, 2H). MS (ES+): 456 (M+H).

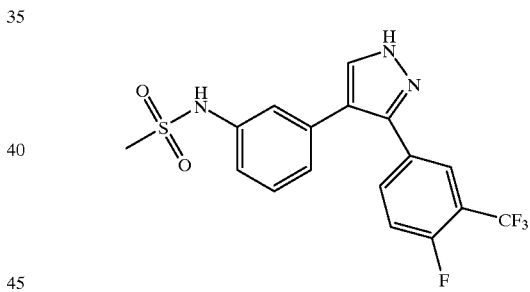

Example 36

Example 36 sets forth the synthesis of a compound having a structure according to formula 1, in which $R^1$ is H, X is 3-methanesulfonamide and Y is 3-CF$_3$, 4-F.

The title compound was prepared by treating a sample of the compound from Example 34 with methanesulfonyl chloride (1 equiv.) and triethylamine (1 equiv.) in AcOEt at r.t. until the completion of reaction followed by work-up and chromatographic purification.

$^1$H NMR (DMSO) δ 9.69 (s, 1H), 8.02 (bs, 1H), 7.75–7.72 (m, 2H), 7.50 (bs, 1H), 7.33 (t, J=8.0 Hz, 1H), 7.13 (d, J=8.4 Hz, 1H), 7.06 (d, J=6.7 Hz, 2H), 2.90 (s, 3H). MS (ES+): 400 (M+H), MS (ES−): 398 (M−H).

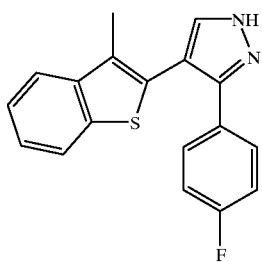

Example 37

Example 37 sets forth the synthesis of a compound having a substituted heteroaryl group and a substituted phenyl group. The title compound was prepared according to the method described in Example 1, with the exception that 3-methyl-2-benzothiophenecarboxaldehyde was substituted for benazaldehyde and 4-fluorophenylacetonitrile was substituted for 3-trifluoromethylphenylacetonitrile.

$^1$H NMR (CDCl$_3$) δ 7.82(d, J=7.5 Hz, 1H), 7.68 (t, J=7.8 Hz, 2H), 7.48 (m, 2H), 7.41–7.36 (m, 2H), 6.96 (t, J=8.7 Hz, 2H), 2.11 (s, 3H). MS (ES+): 309 (M+H), MS (ES−): 307 (M−H).

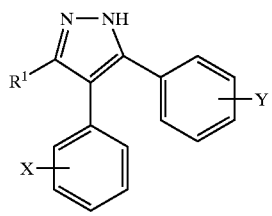

Example 38

Example 38 sets forth the synthesis of a compound having a substituted heteroaryl group and a substituted phenyl group. The title compound was prepared according to the method described in Example 1, with the exception that 3-thiophenecarboxaldehyde was substituted for benazaldehyde and 3-fluorophenylacetonitrile was substituted for 3-trifluoromethylphenylacetonitrile $^1$H NMR (CDCl$_3$) δ 7.64 (bs, 1H), 7.34–7.29 (m, 4H), 7.15 (d, J=4.8 Hz, 1H), 7.04 (t, J=8.7 Hz, 2H). MS (ES+): 245 (M+H), MS (ES−): 243 (M−H).

Example 39

This Example sets forth representative protocols for assaying the antimicrobial activity of selected compounds of the invention.

39.1 IC$_{50}$ Assay

In this assay, buffer (250 mM KCl, 5% Glycerol, 10 mM MgCl$_2$, 0.1 mg/ml bovine serum albumin (BSA)) is combined with 6 mM β-mercaptoethanol, PT5 DNA template, and 1.3 μg/rxn Sigma$^{70}$ saturated *E. coli* RNA Polymerase (obtained from Epicenter). The compound is then added in a manner not to exceed 5% DMSO. Nucleotide triphosphates are then added at the following concentration: 250 μM ATP, CTP and UTP with 100 μM cold CTP and 50 μM α-$^{32}$P CTP. The mixture is incubated for 10 min at about 37° C. A [2×] loading buffer is added and the mixture is then run on a 6% urea denaturing PAGE until bromophenol blue reaches the edge of plate. The gel is soaked (about 20 minutes in 10% MeOH and 10% acetic acid, to remove urea), then dried (about 55 minutes at about 85° C. (BioRad Gel Drier)) and exposed to a Phospho Imaging Plate for 1 hour. The plate is then read on a Fujix Bas1000 Imaging System and quantified using MacBas v2.0 software. An IC50 (in μM) can be calculated as the concentration of a compound of the invention that reduces the enzyme activity to 50% of the control. For the sake of clarity, the above-described assay is used to determine the IC$_{50}$ values referenced in the claims. However, the skilled artisan will recognize that other methods can be used to determine an IC$_{50}$ value.

39.2 Minimum Inhibitory Concentration Assay

For MIC determinations for selected bacteria, log phase growing bacteria are re-suspended at 1×10$^5$ bacteria per mL in LB medium. The compound is added and two-fold dilutions are made. The final volume in the 96-well plate is about 100 μL. The plate is incubated at 37° C. in the dark with shaking. After 16 hours of incubation, growth is monitored by reading A600 or by visual inspection. MIC is defined as the minimum concentration of drug resulting in inhibition of visible growth of bacterial under the conditions described (above) in National Committee for Clinical Laboratory Standards 1993. Methods for dilution antimicrobial susceptibility tests for bacteria that grow aerobically. Approved standard M7-A3; National Committee for Clinical Laboratory Standards: Villanova, Pa.

39.3 Results

The results of the assays on selected compounds of the invention are tabulated below.

TABLE 1

Compounds of Formula 1.

| | | | | 1 |
|---|---|---|---|---|

| | IC$_{50}$[1] | MIC (μM)[1] | | |
|---|---|---|---|---|
| Example | (μM) | B.su | S.au | E.c(tolC) |
| 3 | + | + | + | + |
| 2 | + | ++ | ++ | ++ |
| 1 | + | ++ | ++ | ++ |
| 6 | + | ++ | ++ | ++ |
| 5 | + | ++ | ++ | ++ |
| 4 | + | ++ | ++ | ++ |
| 7 | + | ++ | ++ | ++ |
| 8 | ++ | ++ | ++ | ++ |
| 9 | ++ | ++ | ++ | ++ |
| 10 | ++ | ++ | ++ | ++ |
| 11 | + | ++ | ++ | ++ |
| 12 | + | ++ | ++ | ++ |
| 18 | ++ | ++ | ++ | ++ |
| 19 | ++ | ++ | ++ | ++ |
| 20 | ++ | ++ | ++ | ++ |
| 21 | ++ | ++ | ++ | ++ |
| 22 | ++ | ++ | ++ | ++ |
| 23 | + | + | + | + |
| 24 | ++ | ++ | ++ | ++ |
| 25 | ++ | ++ | ++ | + |
| 26 | ++ | ++ | ++ | ++ |
| 27 | ++ | ++ | ++ | ++ |
| 28 | + | ++ | ++ | ++ |

TABLE 1-continued

Compounds of Formula 1.

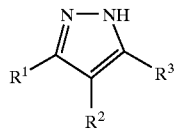

| Example | IC$_{50}$[1] ($\mu$M) | MIC ($\mu$M)[1] B.su | S.au | E.c(tolC) |
|---|---|---|---|---|
| 29 | ++ | ++ | ++ | + |
| 30 | + | ++ | ++ | ++ |
| 31 | ++ | ++ | ++ | + |
| 32 | ++ | ++ | ++ | + |
| 33 | ++ | ++ | ++ | + |
| 34 | ++ | ++ | ++ | ++ |
| 35 | ++ | + | ++ | + |
| 36 | ++ | ++ | ++ | ++ |

[1] (+) ≧ 500 $\mu$M; (++) < 500 $\mu$M

TABLE 2

Compounds of Formula 13.

| Example | IC$_{50}$ ($\mu$M)[1] | MIC ($\mu$M)[1] B.su | S.au | E.c (tolC) |
|---|---|---|---|---|
| 15 | + | ++ | ++ | ++ |
| 16 | + | ++ | ++ | ++ |
| 14 | ++ | ++ | ++ | ++ |
| 17 | ++ | ++ | ++ | ++ |

[1] (+) ≧500 $\mu$M; (++) <500 $\mu$M

TABLE 3

Compounds having a substituted heteroaryl group and a substituted phenyl group.

| Example | IC$_{50}$ ($\mu$M)[1] | MIC ($\mu$M)[1] B.su | S.au | E.c (tolC) |
|---|---|---|---|---|
| 37 | ++ | ++ | ++ | ++ |
| 38 | ++ | ++ | ++ | ++ |

[1] (+) ≧500 $\mu$M; (++) <500 $\mu$M

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula

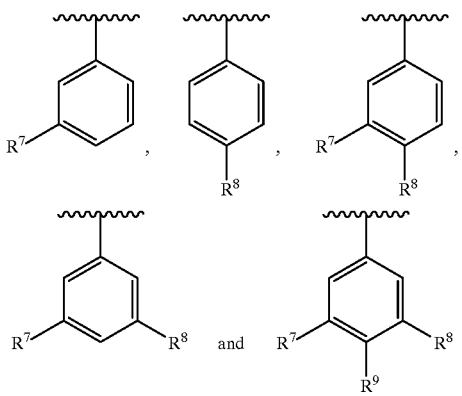

wherein

R$^1$ is selected from the group consisting of H and OR', wherein R' is selected from the group consisitng of H and susbtituted or unsubstituted lower alkyl; and R$^2$ is selected from the group consisting of wherein R$^7$, R$^8$ and R$^9$ are independently selected from the group consisting of hydroxyl, halogen, nitro, cyano, substituted or unsubstituted (C$_1$–C$_6$)alkyl, (C$_1$–C$_6$) haloalkyl, substituted or unsubstituted (C$_1$–C$_6$) heteroalkyl, (C$_1$–C$_6$)alkoxy, (C$_1$–C$_6$)haloalkoxy, (C$_1$–C$_6$)alkylthio, substituted or unsubstituted aryl, substituted or unsubstituted heteroaryl, alkanoyl, alkoxycarbonyl, alkylcarbamoyl, sulfonyl, sulfamoyl and NR$^4$R$^5$, wherein at least one of R$^7$, R$^8$ and R$^9$ is NR$^4$R$^5$;

wherein R$^4$ and R$^5$ are independently selected from the group consisting of hydrogen, substituted or unsubstituted (C$_1$–C$^8$)alkyl, substituted or unsubstituted (C$_1$–C$^8$)heteroalkyl, and one or more of R$^4$ and R$_5$ are substituted or unsubstituted (C$_3$–C$_6$)alkyl or substituted or unsubstituted (C$_3$–C$_6$)heteroalkyl combined with the nitrogen atom to which it is attached to form a four-, five-, six- or seven-membered ring optionally having additional substituents selected from substituted or unsubstituted (C$_1$–C$_8$)alkyl, substituted or unsubstituted (C$_1$–C$_8$)heteroalkyl and substituted or unsubstituted phenyl;

wherein at least one of R$^4$ and R$^5$ is selected from the group consisting of(C$_{1-C8}$)alkyl and (C$_1$–C$_8$) heteroalkyl, comprising a substituent selected from substituted or unsubstituted aryl and substituted or unsubstituted heterocycloalkyl; and R$^3$ is substituted or unsubstituted aryl.

2. The compound of claim 1, wherein at least one of R$^4$ and R$^5$ is selected from the group consisting of (C$_1$–C$_8$)alkyl and $(C_1-C_8)$heteroalkyl, comprising a substituted or unsubstituted heterocycloalkyl substituent.

3. The compound of claim 1, wherein at least one of $R^4$ and $R^5$ is selected from the group consisting of $(C_1-C_8)$alkyl and $(C_1-C_8)$heteroalkyl, comprising a substituted or unsubstituted aryl substituent.

* * * * *